United States Patent
Leynen et al.

(10) Patent No.: US 9,671,722 B2
(45) Date of Patent: Jun. 6, 2017

(54) APPARATUS AND METHOD FOR DETERMINING A MEASURE FOR THE SOLID CONTENT OF A LIQUID TONER, AND PRINTING SYSTEM INCLUDING SUCH AN APPARATUS

(71) Applicant: Xeikon Manufacturing N.V., Lier (BE)

(72) Inventors: Bjorn Leynen, Deurne (BE); Kurt Gustaaf Maria Mampaey, Rumst (BE); Tomas Praet, Rumst (BE)

(73) Assignee: Xeikon Manufacturing N.V., Lier (BE)

( * ) Notice: Subject to any disclaimer, the term of this patent is extended or adjusted under 35 U.S.C. 154(b) by 0 days.

(21) Appl. No.: 15/071,679

(22) Filed: Mar. 16, 2016

(65) Prior Publication Data

US 2016/0274498 A1 Sep. 22, 2016

(30) Foreign Application Priority Data

Mar. 17, 2015 (NL) ...................................... 2014470

(51) Int. Cl.
*G03G 15/10* (2006.01)
*G01L 13/06* (2006.01)
(Continued)

(52) U.S. Cl.
CPC ............ *G03G 15/105* (2013.01); *G01L 13/06* (2013.01); *G01N 9/26* (2013.01); *G01N 15/06* (2013.01);
(Continued)

(58) Field of Classification Search
CPC .......... G03G 15/105; G01N 9/26; G01N 9/36; G01N 15/06; G01N 2015/0687;
(Continued)

(56) References Cited

U.S. PATENT DOCUMENTS

| 4,140,007 A | * | 2/1979 | Bosland | G01N 15/06 73/61.67 |
| 6,687,643 B1 | * | 2/2004 | Cason, Jr. | G01F 23/164 361/283.4 |

(Continued)

FOREIGN PATENT DOCUMENTS

| BE | WO 2012120122 A1 | * | 9/2012 | ............... G01N 9/26 |
| DE | 10064010 A1 | * | 7/2002 | ............... G01N 9/26 |

(Continued)

*Primary Examiner* — Robert Beatty
(74) *Attorney, Agent, or Firm* — The Webb Law firm (57) ABSTRACT

A measurement apparatus for determining a measure for the solid content of a liquid toner. The liquid toner includes a carrier liquid with marking particles, and the solid content is the ratio of the mass of the marking particles divided by the mass of the liquid toner. The measurement apparatus includes a measurement space for receiving liquid toner. The measurement space includes at least one hydrostatic pressure sensor configured and arranged for measuring data representative for the hydrostatic pressure caused by the liquid toner at least one predetermined position in the measurement space. The measurement apparatus also includes a controller configured for receiving the measured data and for determining a measure for the solid content of the liquid toner based on the received data.

17 Claims, 6 Drawing Sheets

(51) Int. Cl.
    *G01N 9/26*     (2006.01)
    *G03G 15/11*    (2006.01)
    *G01N 15/06*    (2006.01)

(52) U.S. Cl.
    CPC ..... *G03G 15/11* (2013.01); *G01N 2015/0687* (2013.01)

(58) Field of Classification Search
    CPC ... G01N 2015/0668; G01L 13/06; G01L 9/00; G01L 7/00; G01G 17/04; G01G 17/06
    USPC ..... 399/57, 62, 237; 74/61.47, 61.71, 61.78, 74/438; 118/689, 692
    See application file for complete search history.

(56) References Cited

U.S. PATENT DOCUMENTS

| | | | |
|---|---|---|---|
| 2001/0054308 A1* | 12/2001 | Komiya | G01N 9/26 73/61.71 |
| 2003/0172723 A1* | 9/2003 | Sato | G01N 7/00 73/61.47 |
| 2009/0052948 A1 | 2/2009 | Ozerov | |
| 2016/0011137 A1* | 1/2016 | Hoefnagels | G01N 27/226 324/663 |

FOREIGN PATENT DOCUMENTS

| | | | |
|---|---|---|---|
| JP | 10149030 A | * | 6/1998 |
| JP | 11065297 A | * | 3/1999 |
| JP | 2002267587 A | * | 9/2002 |
| JP | 2002278300 A | | 9/2002 |
| JP | 2004117687 A | | 4/2004 |

\* cited by examiner

APPARATUS AND METHOD FOR DETERMINING A MEASURE FOR THE SOLID CONTENT OF A LIQUID TONER, AND PRINTING SYSTEM INCLUDING SUCH AN APPARATUS

CROSS-REFERENCE TO RELATED APPLICATION

This application claims priority to Netherlands Patent Application No. 2014470 filed Mar. 17, 2015, the disclosure of which is hereby incorporated in its entirety by reference.

FIELD OF INVENTION

The field of the invention relates to a measurement apparatus for determining a measure for the solid content of a liquid toner, said liquid toner comprising a carrier liquid in which marking particles are dispersed, to a printing system comprising such an apparatus, and to a method for determining a measure for the solid content of a liquid toner.

BACKGROUND

Typical prior art measurement systems for determining the solid content of a liquid toner use solid content sensors. Such solid content sensors have the problem that the sensor may become clogged or blocked when in use.

SUMMARY

An object of the embodiments of the invention is to provide an improved measurement apparatus and method for determining a measure for the solid content of a liquid toner, which apparatus and method allow for an accurate determination of the solid content while avoiding the obstruction or clogging problems of the prior art apparatus and methods.

According to a first aspect of the invention there is provided a measurement apparatus for determining a measure for the solid content of a liquid toner, said liquid toner comprising a carrier liquid with marking particles. The solid content is the ratio of the mass of the marking particles divided by the mass of the liquid toner. The measurement apparatus comprises a measurement space for receiving liquid toner, said measurement space comprising at least one hydrostatic pressure sensor configured and arranged for measuring data representative for the hydrostatic pressure caused by the liquid toner at least one predetermined position in the measurement space; and a controller configured for receiving the measured data and for determining a measure for the solid content of the liquid toner based on the received data.

By using a hydrostatic pressure sensor, the hydrostatic pressure and hence the density can be determined taking into account that the location of the pressure sensor is known. Further for liquid toners, the solid content of a liquid toner can be accurately determined when the density is known. Such a measurement apparatus has the advantage of being very robust while at the same time providing accurate results.

In a preferred embodiment the measurement apparatus further comprises a liquid toner reservoir storing the liquid toner. The liquid toner reservoir is provided with an outlet line for discharging liquid toner into said measurement space and with a return line for receiving liquid toner from said measurement space. The outlet line or the return line may include a pump. Preferably, the controller is configured for controlling the pump such that normal pump operation is stopped or pump power is reduced while measuring data with the at least one hydrostatic pressure sensor, and more preferably such that normal pump operation is stopped or pump power is reduced a predetermined period of time before the measuring of data with the at least one hydrostatic pressure sensor is started, and such that the normal pump operation is only restarted after the measuring. Such an embodiment has the advantage that it can be ensured that there is no significant flow in the measurement space during the measurements, leading to more accurate measurement results.

In a preferred embodiment the measurement space comprises a measurement column with a bottom end comprising an inlet for receiving the liquid toner and with an open top end in contact with the atmosphere. Preferably, the at least one hydrostatic pressure sensor is located in said measurement column at a distance of said open top end, more preferably near the bottom end. In that way it can be ensured that the height of the liquid column above the hydrostatic pressure sensor is sufficient for providing an accurate measurement result. In such an embodiment the measurement space may further comprise an overflow reservoir for receiving liquid toner flowing over said open top end.

In a preferred embodiment the measurement space has a height which is larger than 20 cm, and has a cross section with a largest dimension which is smaller than 10 cm.

In a possible embodiment, the at least one sensor comprises a first sensor at a first position and a second sensor at a second position, said first and second position being in the liquid toner at a first height and a second height of a liquid column, respectively. By performing two measurements the accuracy of the measurements may be further improved. Also such a set-up will allow the measurement space to be closed, i.e. not vented.

According to an alternative embodiment the measurement space is provided in a liquid toner reservoir storing liquid toner; and the measurement space is in fluid communication with the liquid toner reservoir.

The liquid toner reservoir may be provided with a stirring means. In an embodiment where the measurement space is within the liquid toner reservoir the controller may be configured for stopping the normal stirring operation performed by the stirring means or reducing the stirring power of the stirring means a predetermined period of time before the measuring of data with the at least one hydrostatic pressure sensor is started, and such that the normal stirring operation is only restarted after the measuring.

According to an exemplary embodiment the measurement space is delimited by a first electrode and a second electrode, and the measurement apparatus further comprises characterizing means configured for determining a measure for the conductivity of the liquid toner based on a voltage applied between the first and the second electrode or based on a current sent through the liquid toner between the electrodes.

According to another aspect of the invention there is provided a printing system comprising a printing apparatus with a toner feed unit and a toner recuperation line, and a measurement apparatus according to any one of the previous embodiments, wherein the liquid toner reservoir of said measurement apparatus has an outlet for carrying stirred liquid toner to the printing apparatus, and an inlet; said outlet being connected to the toner feed unit of the printing apparatus, and said inlet being connected to the toner recuperation line. In other words the liquid toner reservoir provides the liquid toner for the printing apparatus and receives recycled liquid toner from the printing apparatus.

The toner feed unit may comprise e.g. a feed reservoir and a feed roller which is fed by liquid toner in the feed reservoir. The toner recuperation line may collect any liquid toner from the printing apparatus that needs to be stirred, e.g. liquid toner from the feed reservoir as well as any excess toner from the printing apparatus, e.g. excess toner that is removed from the feed roller or from the developer roller during printing.

The printing system may further comprise at least one of the following: a carrier liquid reservoir for storing carrier liquid, said carrier liquid reservoir being connected via a carrier liquid dosing unit to an inlet of the liquid toner reservoir; a toner concentrate reservoir for storing a concentrated toner liquid; said toner concentrate reservoir having an outlet which is connected via a toner concentrate dosing unit to an inlet of the liquid toner reservoir. The controller may then be configured for controlling at least one of said carrier liquid dosing unit, and said toner concentrate dosing unit in function of the determined measure of the solid content of the liquid toner in the measurement space.

In the context of embodiments of the present invention the carrier liquid reservoir stores carrier liquid, possibly with additives, but preferably without dispersion agent and without marking particles. The toner concentrate reservoir stores a concentrated liquid toner, which is a liquid toner having a higher weight percentage of marking particles than the liquid toner stored in the liquid toner reservoir. The liquid toner and the concentrated liquid toner are typically a dispersion of marking particles in a carrier liquid.

In an exemplary embodiment the liquid toner reservoir and/or the measurement space may comprise at least one further measurement sensor, such as a level gauge, a pressure sensor, a temperature sensor, a sensor for measuring a characteristic of the mixture, such as a conductivity sensor for measuring the electric conductivity of the mixture, a viscosity sensor for measuring the viscosity of the mixture, etc. The controller may then be configured for controlling at least one of a dispersion agent dosing unit, a carrier liquid dosing unit, and a toner concentrate dosing unit in function of said at least one further measured property.

In an exemplary embodiment the printing system further comprises a feed reservoir and a return line for returning excess liquid toner to the feed reservoir, wherein the measurement apparatus is included in the return line.

According to yet another aspect there is provided a method for determining a measure for the solid content of a liquid toner, said liquid toner comprising a carrier liquid with marking particles. The method comprises: receiving liquid toner in a measurement space; measuring data representative for the hydrostatic pressure caused by the liquid toner at least one predetermined position in the measurement space; receiving the measured data at a controller and determining a measure for the solid content of the liquid toner based on the received data.

In a preferred embodiment, the method further comprises storing liquid toner in a liquid toner reservoir; discharging liquid toner using a pump into said measurement space, stopping normal pump operation or reducing pump power during the measuring, and returning liquid toner using said pump from said measurement space to the liquid toner reservoir after said measuring.

In a preferred embodiment the measurement space comprises a measurement column with a bottom end comprising an inlet for receiving the liquid toner and with an open top end in contact with the atmosphere; and the hydrostatic pressure is measured at a distance of said open top end.

In a preferred embodiment, the method further comprises storing liquid toner in a liquid toner reservoir while stirring the liquid toner, wherein the measurement space is provided in the liquid toner reservoir; and the controller stops the stirring or reduces stirring power during the measuring, and restarts the stirring after the measuring.

BRIEF DESCRIPTION OF THE FIGURES

The accompanying drawings are used to illustrate presently preferred non-limiting exemplary embodiments of devices of the present invention. The above and other advantages of the features and objects of the invention will become more apparent and the invention will be better understood from the following detailed description when read in conjunction with the accompanying drawings, in which.

DESCRIPTION OF EMBODIMENTS

Figure 1:
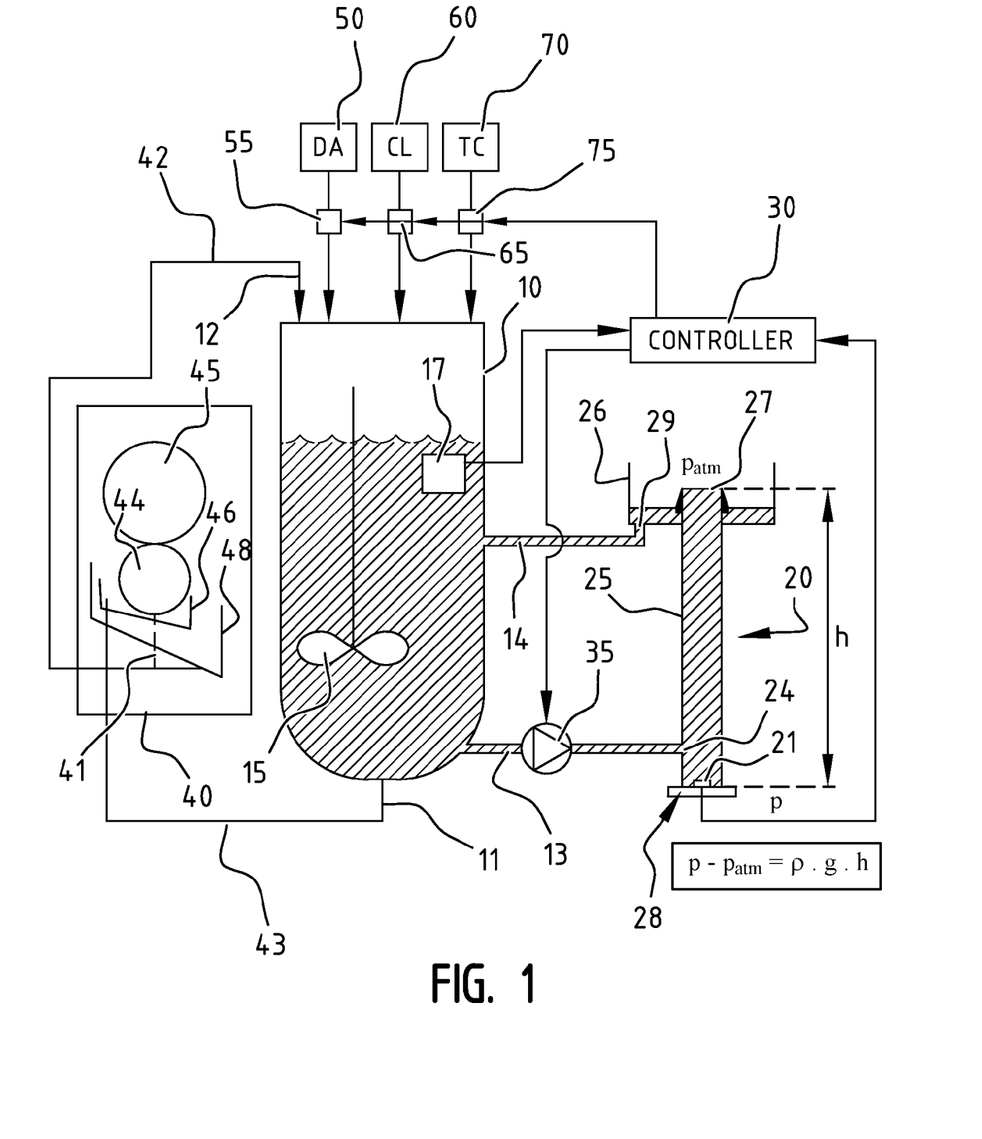
FIG. 1 illustrates schematically an exemplary embodiment of a printing system of the invention.

FIG. 1 illustrates a first exemplary embodiment of a printing system of the invention including a measurement apparatus for determining a measure for the solid content of a liquid toner. The liquid toner comprises a carrier liquid with marking particles.

In xerography processes operating with liquid toner, the imaging particles or marking particles are supplied as solid particles dispersed in a carrier liquid. The imaging particles consist of pigment grains, typically embedded in a small bead of resin. A dispersing agent or dispersant is added to the mix to avoid clustering of the marking particles. Dispersants deflocculate the imaging particles and reduce the viscosity of the liquid toner. The carrier liquid may comprise any suitable liquids as is known in the art, and may include silicone fluids, mineral oils, low viscosity or high viscosity liquid paraffin, isoparaffinic hydrocarbons, fatty acid glycerides, fatty acid esters, vegetable oils, chemically modified vegetable oils, or any combinations thereof. The carrier liquid may further contain variable amounts of charge control agents (CCA), wax, plasticizers, and other additives, although they also can be incorporated into the marking particle itself. The carrier liquid may be volatile or non-volatile. An exemplary digital printing system using liquid toner is described in more detail in US patent application with publication no. 2009/0052948, the content of which is hereby incorporated in its entirety by reference. Typically, the liquid toner may have a solid content between 5% and 60 wt %. The high-shear viscosity, as measured at a shear rate of 3000 s-1 at 25° C. with a cone plate geometry of C60/1° and a gap of 52 µm, is preferably in the range of 5-500 mPa·s.

The measurement apparatus comprises a measurement space 20 for receiving liquid toner. The measurement space comprises a hydrostatic pressure sensor 21 configured and arranged for measuring data representative for the hydrostatic pressure p caused by the liquid toner at a predetermined position in the measurement space. In this exemplary embodiment the position is at the bottom of the measurement space 20, but the skilled person understands that the hydrostatic pressure sensor 21 may also be located at a higher location. However, for accuracy reasons it is preferred to have a liquid column with a minimal height h above the measurement position.

In the embodiment of FIG. 1, the measurement space 20 comprises a measurement column 25 with a bottom end 28 comprising an inlet 24 for receiving fresh liquid toner and with an open top end 27 in contact with the atmosphere. The hydrostatic pressure sensor 21 is located in the measurement column 25 at a distance of said open top end 27, and preferably at or near the bottom end 28. The measurement space 20 further comprises an overflow reservoir 26 for receiving liquid toner flowing over the open top end 27 of the measurement column 25.

The measurement apparatus further comprises a controller 30 configured for receiving the measured data and for determining a measure for the solid content of the liquid toner based on the received data. The density of the liquid toner can be determined from the measured pressure p using the following equation:

$$p - patm = h \cdot \rho \cdot g \quad [1]$$

with
p: hydrostatic pressure at liquid column height h;
p: the atmospheric pressure;
h: the liquid column height at the measurement position of the sensor 21;
ρ: the density of the liquid toner;
g: the gravitational acceleration.

The density ρ of the liquid toner can be expressed in function of the solid content SC, also called solid concentration or mass fraction, i.e. the ratio of the mass of the marking particles divided by the mass of the liquid toner, for a typical liquid toner, using the following equation:

$$\rho = (\rho p \cdot \rho c)/(SC \cdot \rho c + (1 - SC) \cdot \rho p) \quad [2]$$

with ρ the density of the liquid toner, ρp the density of the particles, ρc the density of the carrier liquid, and SC the solid content. In the equation above the influence of the presence of dispersion agent in the liquid toner has not been taken into account as the amount of dispersion agent in the liquid toner is typically very low, and the influence thereof on the equation above is negligible.

Figure 2:
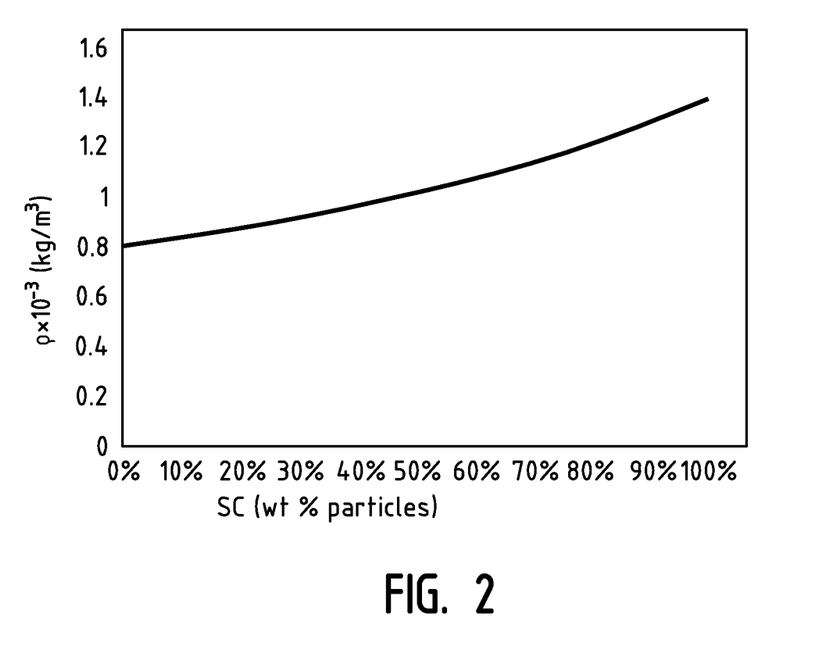
FIG. 2 illustrates a flow chart showing the density in function of the solid content of a liquid toner.

FIG. 2 shows a graph plotting the density ρ. $10^{-3}$ (kg/m$^3$) in function of the solid concentration, also called solid content SC, i.e. ratio of the mass of the marking particles divided by the mass of the liquid toner for a typical liquid toner. The solid content SC may also be expressed in weight percent. Knowing the density ρ of the liquid toner, this graph or equation [2] above allows determining the solid content SC. If the solid content SC is 0.5 (i.e. 50 wt %), this implies that 1 kg of the liquid toner comprises 0.5 kg marking particles.

Further the temperature may be measured and taken into account. If a density ρ1 is measured at temperature T1, then the density ρref at a reference temperature Tref can be calculated using the following formula:

$$\rho ref = \rho 1 + \beta \rho 1 (T1 - Tref) \quad [3]$$

wherein β is the volumetric temperature expansion coefficient of the liquid toner. The density ρref may then be used to calculate the solid content using the graph of FIG. 2 or equation [2] above.

The measurement apparatus further comprises a liquid toner reservoir 10 storing the liquid toner. The liquid toner reservoir 10 is provided with an outlet line 13 for discharging liquid toner into the inlet 24 of the measurement space 20 and a return line 14 for receiving liquid toner from the outlet 29 of the overflow reservoir 26 of the measurement space 20. The outlet line 13 includes a pump 35, and the controller 30 is configured for controlling the pump 35 such that the pump operation is stopped while measuring data with the at least one hydrostatic pressure sensor. Alternatively the power and/or speed of the pump may be reduced. Preferably the controller 30 is configured for controlling the pump 35 such that the pump operation is stopped or such that the power thereof is reduced a predetermined period of time before the measuring of data with the at least one hydrostatic pressure sensor starts, e.g. between 3 and 7 seconds before the measuring starts. In that way any flowing of liquid toner in the measurement space will be avoided or significantly reduced, leading to improved measurement results. The pump 35 remains inoperative until the measuring is finished.

Further the liquid toner reservoir 10 may comprise a stirring means 15, e.g. a stirring means as described in patent application NL 2013779 in the name of the Applicant, the content of which is herein included by reference. There may be provided at least one further measurement device 17 in the liquid toner reservoir 10. The measurement device 17 may be any one or more of the following: a level gauge, a pressure sensor, a temperature sensor, a sensor for measuring a characteristic of the mixture, such as a conductivity sensor for measuring the electric conductivity of the mixture, a viscosity sensor for measuring the viscosity of the mixture. The measurements may be collected by the controller 30 which is configured for controlling at least one of a dispersion agent dosing unit 55, a carrier liquid dosing unit 65, and a toner concentrate dosing unit 75 in function of said measurements, see further.

Preferably, the measurement space has a height which is larger than 20 cm, e.g. between 25 and 45 cm. Preferably, the measurement space has a cross section with a largest dimension which is smaller than 10 cm, e.g. a diameter which is smaller than 10 cm, preferably smaller than 8 cm. Such a height will allow for achieving good measurement results, and the relatively small cross sectional dimensions will avoid that the volume of the measurement space is very big.

The hydrostatic pressure sensor 21 may be any one or more of the following: a pressure transmitter with a pressure port, a pressure transmitter with a flush diaphragm, a submersible pressure transmitter. Preferably the sensor is a pressure transmitter with a flush diaphragm. In other embodiments there may be used a differential pressure transmitter which measures the hydrostatic pressure in the liquid toner as well as the atmospheric pressure patm. Also the hydrostatic pressure sensor 21 may be a so-called hydrostatic level transmitter.

The printing system of FIG. 1 further comprises a printer 40 with a toner feed unit including a feed roller 44, a feed reservoir 46. The printer 40 further comprises a developer roller 45 receiving liquid toner from the feed roller 44, and a recuperation reservoir 48. The liquid toner reservoir 10 has an outlet 11 for discharging stirred liquid toner to the printer 40, and an inlet 12 for receiving recycled liquid toner from the printer 40 via a toner return line 42 coming from the recuperation reservoir 48. The outlet 11 is connected to the toner feed unit of the printer 40, and the inlet 12 is connected to the toner recuperation line 42. Excess liquid toner from the feed roller 44 or from the developer roller 45 or from any further roller (not shown) between the developer roller 45 and the substrate is fed into the recuperation reservoir 48. In order to maintain a good quality liquid toner in the feed reservoir 46 a portion of the liquid toner may be returned to the liquid toner reservoir 10 for stirring, see dashed line 41, and freshly stirred liquid toner may be fed from the liquid toner reservoir 10 back to a feed reservoir 46, see line 43.

The printing system further comprises a carrier liquid reservoir 60 for storing carrier liquid CL, a toner concentrate TC reservoir 70 for storing a concentrated dispersion of marking particles in a carrier liquid, and a dispersion agent reservoir 50 for storing dispersion agent DA. The carrier liquid reservoir 60 is connected via a carrier liquid dosing unit 65 to an inlet of the liquid toner reservoir 10. The toner concentrate reservoir 70 has an outlet which is connected via a toner concentrate dosing unit 75 to an inlet of the liquid toner reservoir 10. The dispersion agent reservoir 50 is connected via a dispersion agent dosing unit 55 to an inlet of the liquid toner reservoir 10. In the context of this embodiment the carrier liquid reservoir 60 stores carrier liquid, possibly with additives, but preferably without dispersion agent and without marking particles. The toner concentrate reservoir 70 stores a concentrated liquid toner, which is a liquid toner having a higher weight percentage of marking particles than the liquid toner stored in the liquid toner reservoir 10. The liquid toner and the concentrated liquid toner are a dispersion of marking particles in a carrier liquid. Both the liquid toner and the concentrated liquid toner comprise carrier liquid, marking particles, and a dispersing agent to disperse the marking particles in the carrier liquid.

The controller 30 is configured for controlling at least one of said carrier liquid dosing unit 65, and said toner concentrate dosing unit 75 in function of the determined measure of the solid content of the liquid toner in the measurement space 20. The controller 30 may be further configured for controlling at least one of a dispersion agent dosing unit 55, a carrier liquid dosing unit 65, and a toner concentrate dosing unit 75 in function of measurements performed by measurement device(s) in the liquid toner reservoir 10.

Figure 3:
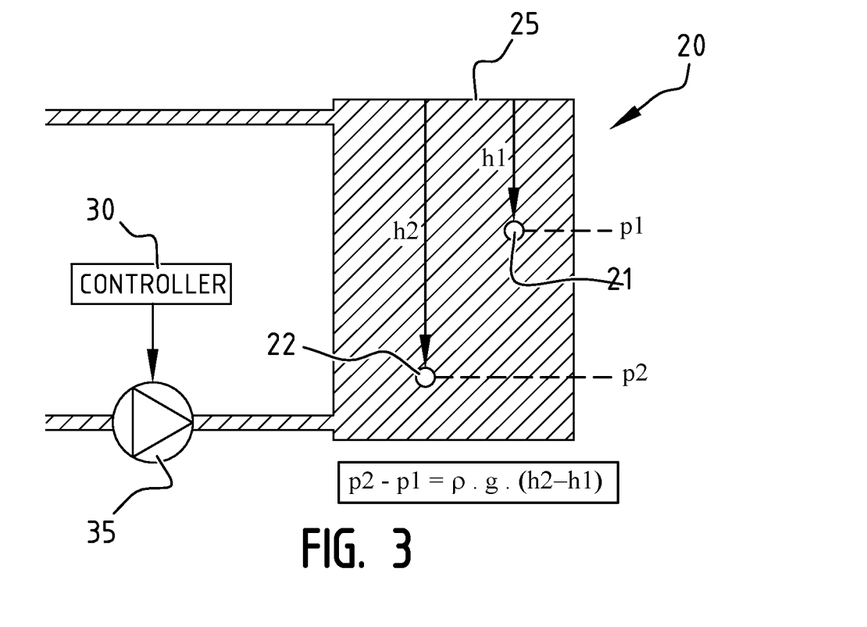
FIG. 3 illustrates schematically an exemplary embodiment of a measurement apparatus.

FIG. 3 illustrates a second embodiment of a measurement apparatus of the invention. In this embodiment the measurement space 20 comprises a gas and liquid tight vessel 25 in which two hydrostatic measurement sensors 21, 22 have been arranged at respective heights h1 and h2 for measuring hydrostatic pressures p1 and p2, respectively. Such a measurement apparatus may be used in a similar manner in the printing system of FIG. 1. In this embodiment the controller 30 is configured for receiving the measured pressure data p1 and p2 and for determining a measure for the solid content of the liquid toner based on the received data. The density of the liquid toner can be determined from the measured pressures p1 and p2 using the following equation:

$$p2-p1=(h2-h1)\cdot\rho\cdot g \qquad [4]$$

with
p2−p1: hydrostatic pressure difference between liquid column height h2 and h1;

h2, h1: the liquid column height at the position of sensors 22 and 21, respectively;
ρ: the density of the liquid toner;
g: the gravitational acceleration.

In this embodiment it is assumed that the measurement space is free of gas. The pump 35 may be controlled in a similar manner as in the embodiment of FIG. 1. It is noted that a pump 35 is not required in all embodiments. In some embodiments the flow may be caused by other means, e.g. by gravity. In such an embodiment there may be provided a valve for interrupting or reducing the flow during the measurements. If the flow rate of the flow through the measurement apparatus is sufficiently low, it may also be envisaged to perform the measurements without interruption of the flow.

Figure 4:
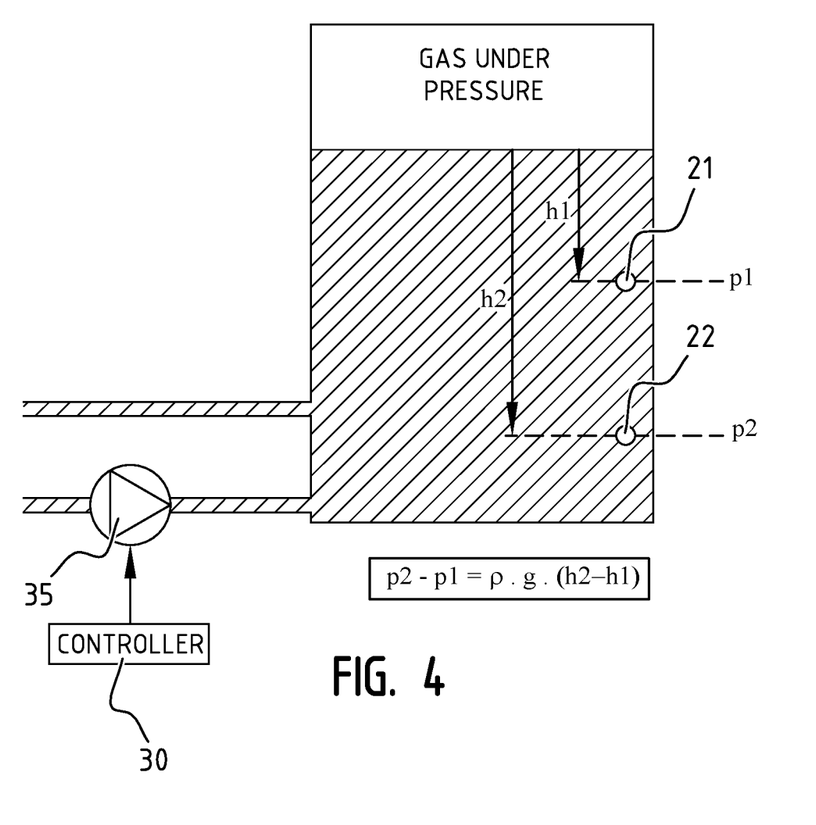
FIG. 4 illustrates schematically an exemplary embodiment of another measurement apparatus.

FIG. 4 illustrates a third embodiment of a measurement apparatus of the invention. This embodiment is similar to the embodiment of FIG. 3, with this difference that a gas is present in the measurement space 20. The skilled person understands that such an embodiment works in the same manner as the embodiment of FIG. 3.

Figure 5:
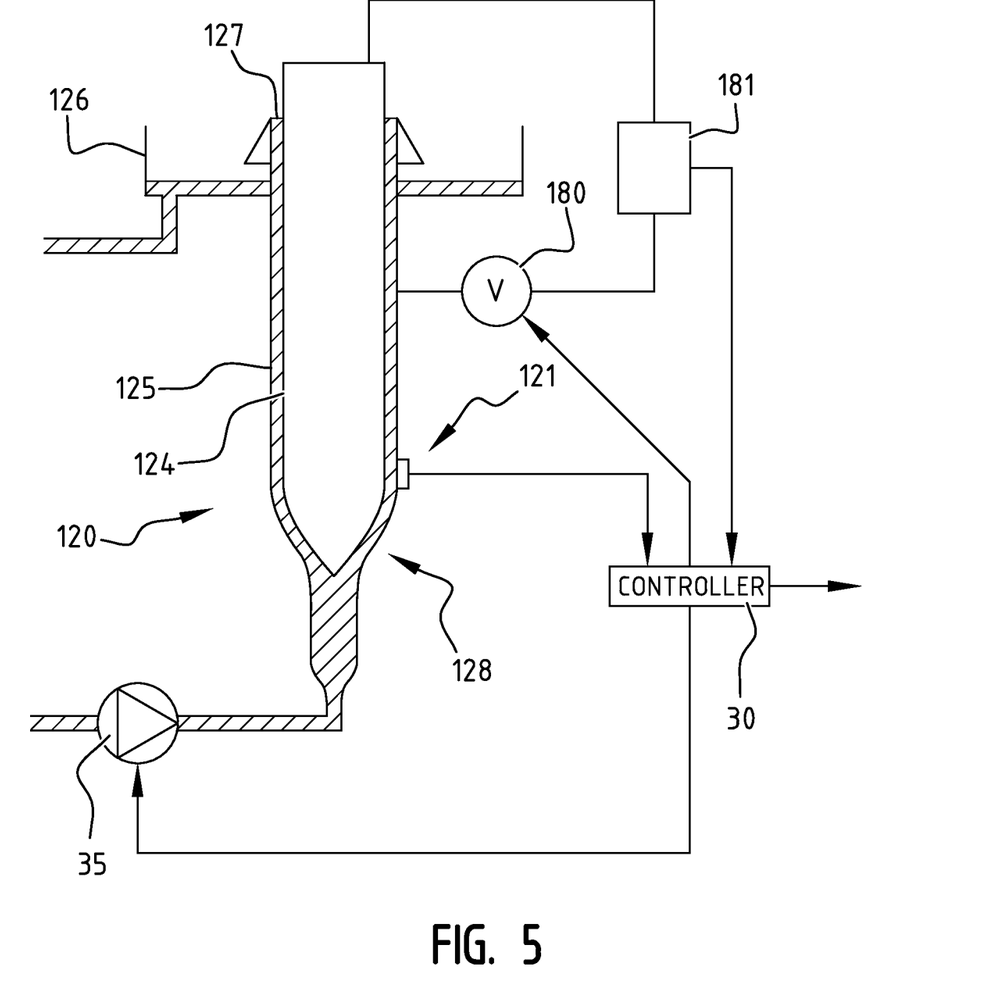
FIG. 5 illustrates schematically an exemplary embodiment of yet another measurement apparatus which further included conductivity measurement means.

FIG. 5 illustrates a fourth embodiment of a measurement apparatus of the invention. In this embodiment the measurement space 120 is formed by a housing in which two electrodes have been integrated. In the illustrated embodiment the housing comprises a cylindrical inner electrode 124 and a cylindrical outer electrode 125, and there is formed a liquid column between the cylindrical inner electrode 124 and the cylindrical outer electrode 125. The housing has an open top end 127 and there is provided an overflow reservoir 126, as in the embodiment of FIG. 1. There is provided a hydrostatic pressure sensor 121 near the bottom end 128 of the measurement space 120. Such a measurement apparatus may be used in a similar manner in the printing system of FIG. 1, with this difference that additional measurements may be performed using the electrodes 124, 125. More in particular, there may be provided a voltage source 180 for applying a voltage across the electrodes 124, 125, and there may be provided measurement means 181 for measuring electrical behavior which is influenced by the properties of the liquid toner flowing in between the electrodes 124, 125. This is described in more detail in patent application EP 14 195 096.4 in the name of the Applicant, the content of which is herein included by reference. It is noted that the electrodes do not have to be cylindrical, and that in all embodiments disclosed in EP 14 195 096.4 in the name of the Applicant, there may be added a hydrostatic sensor 121, preferably near the bottom end of the housing. The measurement data of the measurement means 181 may also be provided to the controller 30 for controlling one or more dosing units 55, 65, 75 as has been described above in connection with FIG. 1.

Figure 6:
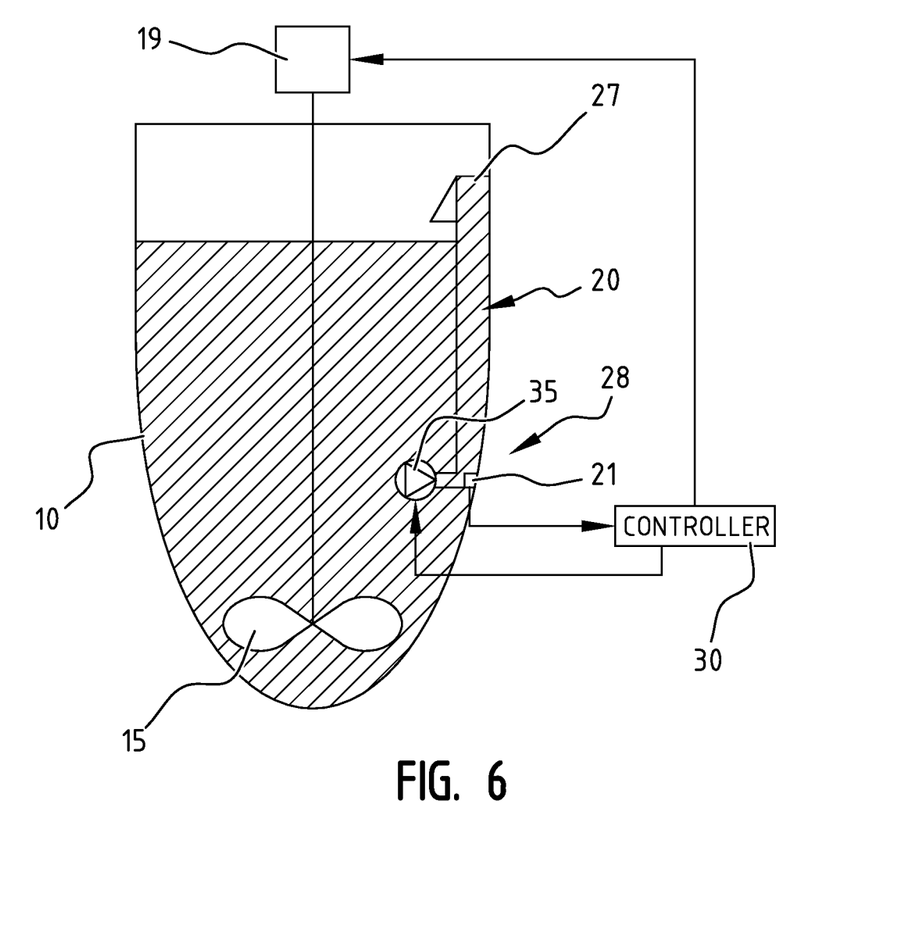
FIG. 6 illustrates schematically an exemplary embodiment of a measurement apparatus which is included in a liquid toner reservoir.

FIG. 6 illustrates a fifth embodiment of a measurement apparatus of the invention. In this embodiment the measurement space 20 is provided in a vented liquid toner reservoir 10 storing liquid toner. The measurement space 20 is in fluid communication with the liquid toner reservoir 10 and comprises a hydrostatic pressure sensor 21 near a bottom end 28 of the measurement space 20. The liquid toner reservoir 10 is provided with a stirring means 15, and the controller 30 is configured for stopping the stirring operation performed by motor 19 of the stirring means 15 a predetermined period of time before the measuring of data with the hydrostatic pressure 21 sensor is started, and such that the stirring operation is only restarted after the measuring. Further there may be provided a pump 35 which is controlled in a similar manner as in the embodiment of FIG. 1. In the illustrated embodiment the measurement space is a column with an open top end extending above the liquid level in the liquid toner reservoir 10, but the skilled person understands that the measurement space may also be embodied e.g. as in FIG. 3 or 4 or 5, wherein the outlet may be above or below the liquid level in the liquid toner reservoir 10.

Figure 7:
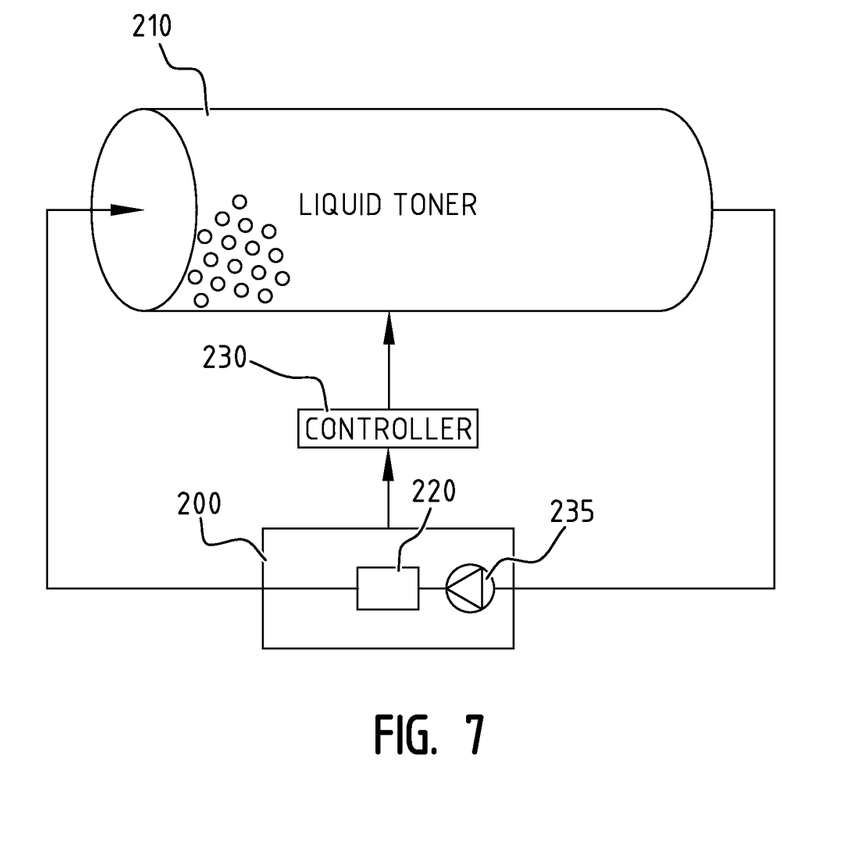
FIG. 7 illustrates an embodiment of a toner preparation apparatus for preparing liquid toner comprising a measurement apparatus according to the invention.

FIG. 7 illustrates an embodiment of a toner preparation apparatus for preparing liquid toner comprising a measurement apparatus 200 according to the invention. The measurement apparatus 200 includes a measurement space 220 and a pump 235, and the measurement space may be configured according to any one of the above disclosed embodiments. The toner preparation apparatus comprises a milling means 210 in the form of a substantially horizontally oriented rotating cylinder, and a controller 230 for controlling the milling means 210 in function of the pressure data measured by the measurement apparatus 200. The controller 230 may be configured to stop the milling means 210. The toner preparation apparatus may further comprise a carrier liquid adding means (not shown), and the controller 230 may be configured to control the carrier liquid adding means in function of the determined measure for the solid content.

While the principles of the invention have been set out above in connection with specific embodiments, it is to be understood that this description is merely made by way of example and not as a limitation of the scope of protection, which is determined by the appended claims.

The invention claimed is:

1. A measurement apparatus for determining a measure for the solid content of a liquid toner, said liquid toner comprising a carrier liquid with marking particles, and said solid content being the ratio of the mass of the marking particles divided by the mass of the liquid toner, said measurement apparatus comprising:
  a measurement space for receiving liquid toner, said measurement space comprising at least one hydrostatic pressure sensor configured and arranged for measuring data representative for the hydrostatic pressure caused by the liquid toner at least one predetermined position in the measurement space; and
  a controller configured for receiving the measured data and for determining a measure for the solid content of the liquid toner based on the received data;
  further comprising a liquid toner reservoir storing the liquid toner; said liquid toner reservoir having an outlet line for discharging liquid toner into said measurement space and a return line for receiving liquid toner from said measurement space;
  wherein the outlet line or the return line includes a pump, and wherein the controller is configured for controlling the pump such that normal pump operation is stopped or such that pump power is reduced while measuring data with the at least one hydrostatic pressure sensor.

2. The measurement apparatus of claim 1, wherein the controller is configured for controlling the pump such that normal pump operation is stopped or pump power is reduced a predetermined period of time before the measuring of data with the at least one hydrostatic pressure sensor is started, and such that the normal pump operation is only restarted after the measuring.

3. The measurement apparatus of claim 1, wherein the measurement space comprises a measurement column with a bottom end comprising an inlet for receiving the liquid toner and with an open top end in contact with the atmosphere; wherein said at least one hydrostatic pressure sensor is located in said measurement column at a distance of said open top end.

4. The measurement apparatus of claim 3, wherein said measurement space further comprises an overflow reservoir for receiving liquid toner flowing over said open top end.

5. The measurement apparatus of claim 1, wherein said measurement space has a cross section with a largest dimension which is smaller than 10 cm.

6. The measurement apparatus of claim 1, wherein the at least one sensor comprises a first sensor at a first position and a second sensor at a second position, said first and second position being in the liquid toner at a first height and a second height of a liquid column, respectively.

7. The measurement apparatus of claim 1, wherein the measurement space is provided in a liquid toner reservoir storing liquid toner; said measurement space being in fluid communication with the liquid toner reservoir.

8. The measurement apparatus of claim 1, wherein said measurement space is a gastight vessel.

9. The measurement apparatus of claim 1, wherein the measurement space is delimited by a first electrode and a second electrode, and the measurement apparatus further comprises characterizing means configured for determining a measure for the conductivity of the liquid toner based on a voltage applied between the first and the second electrode or based on a current sent through the liquid toner between the electrodes.

10. The measurement apparatus of claim 1, further comprising a temperature sensor for sensing a measure for the temperature of the liquid toner in the measurement space, wherein the controller is further configured for taking into account the sensed measure for the temperature when determining the measure for the solid content of the liquid toner based on the received data.

11. A printing system comprising:
  a printing apparatus with a toner feed unit and a toner recuperation line, and
  an apparatus according to claim 1, wherein the liquid toner reservoir of said apparatus has an outlet for discharging stirred liquid toner to the printing apparatus, and an inlet; said outlet being connected to the toner feed unit of the printing apparatus, and said inlet being connected to the toner recuperation line.

12. A measurement apparatus for determining a measure for the solid content of a liquid toner, said liquid toner comprising a carrier liquid with marking particles, and said solid content being the ratio of the mass of the marking particles divided by the mass of the liquid toner, said measurement apparatus comprising:
  a measurement space for receiving liquid toner, said measurement space comprising at least one hydrostatic pressure sensor configured and arranged for measuring data representative for the hydrostatic pressure caused by the liquid toner at least one predetermined position in the measurement space; and
  a controller configured for receiving the measured data and for determining a measure for the solid content of the liquid toner based on the received data;
  wherein said measurement space has a height which is larger than 20 cm.

13. A measurement apparatus for determining a measure for the solid content of a liquid toner, said liquid toner comprising a carrier liquid with marking particles, and said solid content being the ratio of the mass of the marking particles divided by the mass of the liquid toner, said measurement apparatus comprising:
  a measurement space for receiving liquid toner, said measurement space comprising at least one hydrostatic pressure sensor configured and arranged for measuring data representative for the hydrostatic pressure caused by the liquid toner at least one predetermined position in the measurement space;

a controller configured for receiving the measured data and for determining a measure for the solid content of the liquid toner based on the received data;

wherein the measurement space is provided in a liquid toner reservoir storing liquid toner; said measurement space being in fluid communication with the liquid toner reservoir;

wherein the liquid toner reservoir is provided with a stirring means, and wherein the controller is configured for stopping the stirring operation performed by the stirring means a predetermined period of time before the measuring of data with the at least one hydrostatic pressure sensor is started, and such that the stirring operation is only restarted after the measuring.

14. A method for determining a measure for the solid content of a liquid toner, said liquid toner comprising a carrier liquid with marking particles, said solid content being the ratio of the mass of the marking particles divided by the mass of the liquid toner; said method comprising:

receiving liquid toner in a measurement space;

measuring data representative for the hydrostatic pressure caused by the liquid toner at least one predetermined position in the measurement space; and receiving the measured data at a controller and for determining a measure for the solid content of the liquid toner based on the received data;

said method further comprising storing liquid toner in a liquid toner reservoir; discharging liquid toner using a pump into said measurement space, stopping the pump operation during the measuring, and returning liquid toner using said pump from said measurement space to the liquid toner reservoir after said measuring.

15. The method of claim 14, wherein the measurement space comprises a measurement column with a bottom end comprising an inlet for receiving the liquid toner and with an open top end in contact with the atmosphere; wherein the hydrostatic pressure is measured at a distance of said open top end.

16. The method of claim 15, further comprising storing liquid toner in a liquid toner reservoir while stirring the liquid toner, wherein the measurement space is provided in the liquid toner reservoir storing liquid toner; and wherein the controller stops the stirring during the measuring, and restarts the stirring after the measuring.

17. The method of claim 14, further comprising sensing a measure for the temperature of the liquid toner in the measurement space, and taking into account the sensed measure for the temperature when determining the measure for the solid content of the liquid toner based on the received data.

* * * * *

UNITED STATES PATENT AND TRADEMARK OFFICE
CERTIFICATE OF CORRECTION

Page 1 of 1

PATENT NO. : 9,671,722 B2
APPLICATION NO. : 15/071679
DATED : June 6, 2017
INVENTOR(S) : Bjorn Leynen et al.

It is certified that error appears in the above-identified patent and that said Letters Patent is hereby corrected as shown below:

On the Title Page

Column 2, Item (57) ABSTRACT, Line 10, before "at least" insert -- at --

In the Claims

Column 9, Line 39, Claim 1, before "at least" insert -- at --

Column 10, Line 52, Claim 12, before "at least" insert -- at --

Column 11, Line 2, Claim 13, before "at least" insert -- at --

Column 11, Line 26, Claim 14, before "at least" insert -- at --

Signed and Sealed this
Eighth Day of August, 2017

Joseph Matal
*Performing the Functions and Duties of the*
*Under Secretary of Commerce for Intellectual Property and*
*Director of the United States Patent and Trademark Office*